(12) United States Patent
Weinschenk et al.

(10) Patent No.: US 8,399,613 B2
(45) Date of Patent: Mar. 19, 2013

(54) TUMOUR-ASSOCIATED PEPTIDES THAT BIND TO MHC MOLECULES

(75) Inventors: Toni Weinschenk, Esslingen (DE); Hans Georg Rammensee, Tübingen (DE); Stefan Stevanovic, Tübingen (DE)

(73) Assignee: Immatics Biotechnologies GmbH, Tubingen (DE)

( * ) Notice: Subject to any disclaimer, the term of this patent is extended or adjusted under 35 U.S.C. 154(b) by 384 days.

(21) Appl. No.: 12/632,463

(22) Filed: Jan. 22, 2010

(65) Prior Publication Data

US 2010/0184211 A1 Jul. 22, 2010

Related U.S. Application Data

(60) Division of application No. 11/848,062, filed on Aug. 30, 2007, now Pat. No. 7,763,711, which is a division of application No. 10/999,364, filed on Nov. 29, 2004, now Pat. No. 7,396,904, which is a continuation of application No. PCT/EP03/03181, filed on Mar. 27, 2003.

(30) Foreign Application Priority Data

May 29, 2002 (DE) .................. 102 25 144

(51) Int. Cl.
*C07K 7/06* (2006.01)
(52) U.S. Cl. ............ 530/328; 514/21.6; 424/184.1
(58) Field of Classification Search .......... 530/328; 514/21.6; 424/184.1
See application file for complete search history.

(56) References Cited

U.S. PATENT DOCUMENTS

| 4,810,781 | A | 3/1989 | Hollinshead |
| 6,809,179 | B1 | 10/2004 | Konopitzky et al. |
| 7,125,663 | B2 * | 10/2006 | Schlegel et al. ............. 435/6.14 |
| 2002/0007173 | A1 | 1/2002 | Kundig et al. |
| 2003/0170719 | A1 * | 9/2003 | Matsuda et al. ............. 435/7.1 |
| 2003/0170742 | A1 * | 9/2003 | Carman et al. ............. 435/7.2 |

FOREIGN PATENT DOCUMENTS

| WO | 0250103 | 6/2002 |
| WO | 02094981 | 11/2002 |

OTHER PUBLICATIONS

Nagase, T et al. "Human mRNA for KIAA0367 gene, partial cds," GenBank, Database online Oct. 4, 2005; pp. 1-3.
International Search Report for PCT/EP03/03181; mailed Oct. 23, 2003, 6 pages.
Schirle et al., Eur. J. Immunol. (2000) 30:2216-2225.
Parker et al.; "Scheme for Ranking Potential . . . Peptide Side-Chains", Journal of Immunology; XP-00088437; 1994; pp. 163-175.
Park et al, Sequence of MET Protooncogene cDNA . . . receptors:, Proc. Natl. Acad. Sci. USA; XP-000941506; 1978; pp. 6379-6383.
Heid et al. "Adipocyte Differentiation-related . . . membrane", Biochem J.; XP-002060680; 1996, pp. 1025-1030.
Weinschenk et al.; "Integrated Functional . . . Antitumor Vaccines", Cancer Research, vol. 62, Oct. 15, 2002; pp. 5818-5827.
Schirle et al. " Identification of Tumor-Associated . . . Approach", Eur. J. Immunol., vol. 3 30, XP-002246625; 2000; pp. 2216-2225.
Schmidt et al. "Induction of Adipophilin-Specific . . . Cell Lysis", Cancer Research, vol. 64, Feb. 1, 2004; pp. 1164-1170.
Renner et al. An. Hematol. 80; 255-266; 2001.

* cited by examiner

*Primary Examiner* — David Lukton
(74) *Attorney, Agent, or Firm* — Baker Donelson Bearman, Caldwell & Berkowitz, PC

(57) ABSTRACT

The invention relates to a tumor-associated peptide containing an amino sequence, which is selected from the group consisting of SEQ ID NO:1 to SEQ ID NO:79 of the enclosed listing. The peptide has the ability to bind to a molecule of the human major histocompatibility complex (MHC) class-I. The invention also relates to the use of the peptides for manufacture of a medicament and for treating tumorous diseases. The invention further relates to a pharmaceutical composition, which comprises at least one of the peptides.

13 Claims, 7 Drawing Sheets

TUMOUR-ASSOCIATED PEPTIDES THAT BIND TO MHC MOLECULES

CROSS REFERENCE TO RELATED APPLICATIONS

This is a Divisional Application of U.S. patent application Ser. No. 11/848,062 filed Aug. 30, 2007 now U.S. Pat. No. 7,763,711 which is a divisional of U.S. patent application Ser. No. 10/999,364, now U.S. Pat. No. 7,396,904, filed Nov. 29, 2004, which is a continuation application of International Patent Application PCT/EP 03/03181, filed Mar. 27, 2003, designating the United States and published in German as WO 03/102023 A1, which claims priority to German Application Number 102 25 144.4, filed May 29, 2002, the contents of each are incorporated herein by reference in their entireties.

TECHNICAL FIELD

The present invention relates to tumor-associated peptides having the ability to bind to a molecule of human major histocompatibility (MHC), class I.

Such peptides are used—for example—in immunotherapy of tumor-associated diseases.

BACKGROUND ART

When tumor cells are eliminated by the immune system the identification of tumor-associated antigens (TAA) by components of the immune system plays a pivotable role. This mechanism is based on the fact that there exist qualitative or quantitative differences between tumor cells and normal cells. To induce an anti-tumor-response, the tumor cells have to express antigens which induce an immune response being sufficient for the elimination of the tumor.

In particular, CD8-expressing cytotoxic T-lymphocytes (in the following CTL) are involved in rejection of tumors. To induce such an immune reaction by cytotoxic T-cells foreign proteins/peptides have to be presented to T-cells. Antigens are recognized as peptide fragments by T-cells only if they are presented by MHC-molecules on cell surfaces. These MHC ("major histocompatibility complex") molecules are peptide receptors which normally bind peptides intracellularly and transport them to the cell surface. This complex of peptide and MHC-molecule is recognized by T-cells. Human MHC-molecules are also designated as human leukocyte antigens (HLA).

There are two classes of MHC-molecules: MHC class-I-molecules, which are present on most cells having a nucleus, present peptides generated by degradation of endogenous proteins. MHC class-II-molecules are present on professional antigen-presenting cells (APC) only and present peptides of exogenous proteins, which are taken up and processed by APC during endocytosis. Peptide/MHC-class-I complexes are recognized by CD8-positive cytotoxic T-lymphocytes, peptide/MHC class-II-complexes are recognized by CD4 helper T-cells.

In order to induce a cellular immune response a peptide has to bind to a MHC-molecule. This action depends on the allele of the MHC-molecule and on the amino acid sequence of the peptide. MHC-class-I-binding peptides, being—as a general rule—of 8 to 10 residues in length, comprise two conserved residues ("anchor") in their sequence, that engage complementary pockets located in the MHC-molecule.

In order for the immune system to induce an effective CTL-response directed against tumor-associated peptides, these peptides have not only to be able to bind to specific MHC-class-I-molecules expressed by tumor cells but have also to be able to be recognized by T-cells having specific T-cell receptors (TCR).

When developing a tumor vaccine a main aim is to identify and to characterize tumor-associated antigens which are recognized by CD8+ CTL.

The antigens—or their epitopes, respectively—which are recognized by tumor-specific cytotoxic T-lymphocytes can be molecules of all classes of proteins, such an enzymes, receptors, transcription factors, etc. Another important class of tumor-associated antigens are tissue-specific structures such as the cancer-testis antigens, which are expressed in various kinds of tumors and healthy testis tissue.

In order for the T-lymphocytes to identify proteins as tumor-specific antigens and in order to use them in therapy, certain requirements have to be met: The antigen has to be expressed mainly by tumor cells and not by normal cells or at least to a minor extent as in tumors. Further, it is desirable if the specific antigen is present not only in one kind of tumor but also in other kinds in high concentrations. Further, the presence of epitopes in the amino acid sequence of the antigen is essentially since those peptides derived from tumor-associated antigens are supposed to induce a T-cell-response, either in vitro or in vivo.

Thus, TAA represent a starting point for developing a tumor vaccine. Methods for identification and characterization of TAA are based on the utilization of patient-derived CTL or on the generation of differential transcription profiles between tumors and normal tissue.

Identification of genes which are overexpressed in tumorous tissues or which are selectively expressed in such tissues does not provide precise information about utilization of antigens transcribed from these genes for immune therapy. This is based on the fact that only several epitopes of these antigens are suitable for such an utilization since a T-cell response is induced—via MHC presentation—by epitopes of the antigens only and not by the antigen as a whole. Thus it is important to select those peptides of overexpressed or selectively expressed proteins, that are presented by MHC-molecules, thereby generating points of attack for specific tumor recognition by cytotoxic T-lymphocytes.

DISCLOSURE OF THE INVENTION

In view of the above it is an object of the present invention to provide at least one new amino acid sequence of such a peptide which can bind to a molecule of the human major histocompatibility complex (MHC)-class-I.

This object is achieved, according to the invention, by providing a tumor-associated peptide containing an amino acid sequence which is selected from the group consisting of SEQ ID NO:1 to SEQ ID NO:79 of the enclosed sequence listing, the peptide having the ability to bind to a molecule of the human major histocompatibility complex (MHC)-class-I.

The object underlying the invention is completely achieved in that way.

It is understood that peptides identified from the tumor may be synthesized or be expressed in cells in order to obtain larger amounts and in order to utilize them for purposes described below.

The inventors were able to identify the above-mentioned peptides as specific ligands of MHC-class-I-molecules from tumorous tissue. In this connection, with the term "tumor-associated", peptides are denoted herein, which have been isolated and identified from tumorous material. These peptides—being presented on genuine (primary) tumors—are subject to antigen processing in a tumor cell.

The specific ligands can be used in cancer therapy, for example to induce an immune response directed against tumor cells, which express the corresponding antigens from which the peptides derive.

On the one hand, such an immune response in terms of an induction of CTL can be achieved in vivo. For that purpose a peptide is administered—for example in form of a pharmaceutical composition—to the patient, who suffers from a tumor disease associated with the TAA.

On the other hand, a CTL-response against a tumor expressing the antigen from which the peptides derive can be induced ex vivo. For this purpose the CTL-precursor cells are incubated together with antigen-presenting cells and the peptides. The CTL stimulated thereby are then cultivated, and these activated CTL are administered to the patient.

A further possibility is to load APC ex vivo with the peptides and to administer those loaded APC to a patient, who, in tumor tissue, expresses the antigen from which the peptide is derived. The APC can in turn present the peptide to the CTL in vivo and activate them.

The peptides according to the invention can further be utilized as diagnostic reagents.

In that way, the peptides can be used to find out if, in a CTL population, there exist CTL specifically directed against the peptide or if the CTL were induced by a therapy.

Further, the increase of precursor T-cells, which show reactivity against the defined peptide, can be tested with the peptide.

In addition, the peptide can be used as a marker to assess the disease course of a tumor expressing the antigen from which the peptide derives.

In the enclosed Table 1, the identified peptides are listed. They are disposed according to the respective HLA-types they are binding to. Further, in the table the proteins are disposed, from which the peptide is deriving, and the respective position of the peptide in the corresponding protein. In doing so, the English denotation of the proteins was kept to avoid misleading translations. Further, the Acc-numbers are quoted, which are listed in the gene bank of the "National Center for Biotechnology Information" of the National Institute of Health.

The inventors were able to isolate the peptides (or ligands) from renal cell carcinomas of two patients, RCC01 and RCC13. In doing so, 68 ligands from tumorous tissue of patient RCC01 were isolated and 13 ligands from tumorous tissue of patient RCC13. Two of the ligands identified in both patients were identical. Those were the peptides having the sequence ID No. 1 and 3 (YVDPVITSI of met-protooncogene (C-Met) and ALLNIKVKL of keratin 18).

79 ligands could be identified from the tumors of the patients, 30 of which were bound to the HLA-subtypes HLA-A*02, 13 were bound to HLA-A*68, 34 to HLA-B*18 or HLA-B*44 and 2 to HLA*24.

HLA-A*02-ligands were all exhibiting the allele-specific peptide motif: (Leucine/Valine, Isoleucine, Alanine or Methionine on position 2; Leucine/Valine, Isoleucine or Alanine at the C-terminus.

Some of the ligands derived from abundantly expressed so-called housekeeping genes, which are expressed equally in most tissues, but many were distinguished by tumor-association.

The peptide having the sequence ID No. 1 YVDPVITSI, for example, is concerning a ligand, which, in particular, is associated with tumors and which derives from the met-protooncogene (c-Met) (position 654-662). Peptides having the sequence ID Nos. 2, 22 and 23 derive from adipophilin (also denoted as "adipose differentiation related" protein) and comprise positions 129-137, 62-71 and 349-358 in this protein, whereby the last two are among HLA-A*68 presented peptides. The ligand having the sequence ID No. 3 is a ligand, which is derived from keratin 18 and is located at position 365-373.

The major part of the ligands was comprising the amino acid glutamic acid (E) on position 2, which is an anchor-amino acid of the HLA-B*44-subtype. In that way, peptides could be identified, which derive from proteins, that have proven to be immunogenic in earlier experiments, for example peptide having sequence ID No. 5, which derives from protein Annexin II (position in Annexin 55-63). This protein proved to be immunogenic in respect of MHC class-II-molecules in melanoma patients (see Heinzel et al., The self peptide annexin II (208-223) presented by dendritic cells sentisizes autologous CD4+ T-lymphocytes to recognize melanoma cells, 2001, Cancer Immunol. Immunother. 49: 671-678).

Further, some peptides could be identified, which derive from proteins, that are, in particular, overexpressed in tumorous tissue. Thus, fragments of Vimentin (EEIAFLKKL, position 229-237) and Caldesmon (DEAAFLERL, position 92-100) could be identified. Young et al., Expression profiling of renal epithelial neoplasms: a method for tumor classification and discovery of diagnostic molecular markers, 2001, Am. J. Pathol., 158: 1639-1651) disclosed that these proteins were overexpressed in renal cell carcinoma tissues.

The inventors were further able—among other things—to identify ligands, which derived from ets-1 (NEFSLKGVDF, position 86-95), Alpha-Catenin (NEQDLGIQY, position 169-177) and Galectin 2 (SEVKFTVTF, position 80-88).

The inventors further isolated fragment YYMIGEQKF (sequence ID No. 79) which derives from the enzyme Nicotinamid-N-Methyltransferase (position 203-211). Takahashi et al., Gene expression profiling of clear cell renal cell carcinoma: gene identification and prognostic classification, 2001, Proc. Natl. Acad. Sci. USA, 98: 9754-9749, disclosed that this enzyme was overexpressed in renal cells carcinoma.

Surprisingly, the inventors were able to detect cytotoxic T-lymphocytes specific for one of the identified peptides in donor blood. Thus, it is possible to induce a CTL-response specific against the tumors.

The inventors were able to demonstrate, in their own experiments, that by using two exemplarily selected peptides cytotoxic T-lymphocytes (CTL) could be generated in vivo, which were specific for peptides having sequence ID No. 1 (c-Met-protoocogene-fragment or c-Met-peptide) or specific for the peptide having the sequence ID No. 2 (adipophilin fragment or adipophiline peptide). These CTL were able to specifically kill tumor cells, which expressed the respective proteins and which derived from different tumor cell lines of different patients. The inventors could further demonstrate that with the mentioned CTL dendritic cells, for example, could be lysed, which were previously pulsed (loaded) with the respective peptides. The inventors demonstrated with these experiments that human T-cells can be activated in vitro by using the peptides according to the invention as epitopes. The inventors could not only demonstrate that CTL, which were obtained from peripheral blood mononuclear cells (PB-MNC) of a patient and which were specific for a certain peptide, were able to kill cells of the same kind of tumor of another patient. The inventors further demonstrated that even cells of other kinds of tumors could be lysed with these CTL.

A further object of the invention relates to peptides, which may be used for stimulation of an immune response, too, which comprise sequence ID No. 1 to 79 and in the sequence of which at least one amino acid may be replaced by another amino acid with similar chemical features.

With respect to the respective MHC-subtypes, these are, for example, anchor amino acids, which may be replaced by amino acids with similar chemical features. For example, in peptides, which are associated with MHC-subtype HLA-A*02, Leucine on position 2 may be replaced with Isoleucine, Valine or with Methionine and vice versa, and Leucine at the C-terminus with Valine, Isoleucine and Alanine, which all comprise non-polar side chains.

Further, it is possible to use peptides having sequence ID Nos. 1 to 79, which comprise at least one additional amino acid at the N- or C-terminus, or in the sequence of which at least one amino acid may be deleted.

Further, peptides having sequence ID Nos. 1 79 can be used, which comprise at least one amino acid being chemically modified.

The varying amino acid(s) is (are) chosen in that way that the variation does not effect the immunogenity of the peptide, that is the peptide still displays a similar binding affinity to the MHC-molecule and the ability to stimulate T-cells.

According to the invention, the peptide can be used for treatment of tumor diseases and/or adenomatous diseases.

Tumor diseases to be treated comprise, for example, renal, breast, pancreas, gastric, testis and/or skin cancer. Listing of tumor diseases is supposed to be merely illustrative and shall not limit the scope of usage.

The inventors were able to demonstrate, in their own experiments, that the peptides according to the invention are suitable for such use. Thus, it was demonstrated that with specifically generated CTL, which were specific for certain peptides, tumor cells could be effectively and selectively killed.

To use tumor-associated antigens in a tumor vaccine there are, as a general rule, several possible forms of application. Tighe, et al., 1998, Gene vaccination: plasmid DNA is more than just a blueprint, Immunol. Today 19(2): 89-97, demonstrated that the antigen could be administered either as recombinant protein with suitable adjuvants or carrier systems or—in plasmid vectors—as cDNA encoding the antigen. In the latter cases, to induce an immune response, the antigen has to be processed and presented by antigen-presenting cells (APC) in the patient's body.

Melief, et al., 1996, Peptide-based cancer vaccines, Curr. Opin. Immunol. 8: 651-657, demonstrated a further possibility, i.e., to use synthetic peptides as vaccine.

A further object of the invention relates to the peptide, which can be used in combination with adjuvants, or on its own.

As an adjuvant, the granulocyte-macrophage-colony-stimulating-factor (GM-CSF) can be used, for example.

Further examples for such adjuvants are aluminumhydroxide, emulsions of mineral oils, such as Freund's adjuvants, saponines or silicon compounds.

Use of adjuvants is of advantage, since the immune response induced by the peptide can be boosted and/or the peptide can be stabilized.

Another object of the invention relates to the peptide, which is administered when bound to an antigen-presenting cell.

This step is advantageously since the peptides can be presented to the immune system, in particular to cytotoxic T-lymphocytes (CTL). In that way, CTL can identify and specifically kill the tumor cells. For example, dendritic cells, monocytes or B-lymphocytes are suitable as antigen-presenting cells for that purpose.

In doing so, the cells are, for example, loaded with the peptides ex vivo. On the other hand, the cells may be transfected with DNA or the corresponding RNA encoding the peptides in order for the peptides being expressed on the cells.

The inventors were able to demonstrate, in their own experiments, that dendritic cells (DC) could be loaded with specific peptides and that these loaded dendritic cells activated peptide-specific CTL. That means that the immune system can be stimulated to produce CTL directed against the tumors which express the respective peptides.

The antigen-presenting cells carrying the peptide may be used either in a direct manner or may be activated with heat shock protein gp96 prior use. This heat shock protein induces expression of MHC-class-I-molecules and of costimulating molecules such as B7, and, in addition, stimulates production of cytokins. In that way the induction of immune responses is enhanced all in all.

Yet another object of the invention relates to peptides, which are used to label leukocytes, in particular T-lymphocytes.

This use is of advantage, if the peptides are used, in a CTL-population, to detect CTL specifically directed against the peptides.

The peptide can further be used as a marker to assess a therapy course of a tumor disease.

The peptide can also be used for monitoring therapy in other immunizations or therapies. In that way the peptide may not only be used in a therapeutical way but also in a diagnostic way.

A further object of the invention relates to the peptides, which are used for generating an antibody.

Polyclonal antibodies can be obtained, in a general manner, by immunization of animals by means of injection of the peptides and subsequent purification of the immunoglobuline.

Monoclonal antibodies can be generated according to standardized protocols, for example as described in Methods Enzymol. (1986), 121, Hybridoma technology and monoclonal antibodies.

A further object of the invention relates to a pharmaceutical composition comprising one or more peptides.

This composition may for example be applied parenterally, for example subcutaneously, intradermally or intramuscularly or may be administered orally. In doing so the peptides are dissolved or suspended in a pharmaceutically acceptable carrier, preferably an aqueous carrier. The composition can further comprise additives, for example, buffers, binders, diluents etc.

The peptides can also be administered together with immunostimulating substances, for example cytokines. An extensive description of additives which can be used in a composition of this nature is given, for example, in A. Kibbe, Handbook of Pharmaceutical Excipients, 3. ed., 2000, American Pharmaceutical Association and pharmaceutical press.

The composition may be used for prevention, prophylaxis and/or therapy of tumor diseases and/or adenomatous diseases.

The pharmaceutical composition comprising at least one of the peptides having sequence ID Nos. 1 to 79 is administered to a patient who suffers from a tumor disease, the respective peptide or antigen is associated with. Thereby, a tumor-specific immune response can be induced on basis of tumor-specific CTL.

The amount of the peptide or of the peptides being present in the pharmaceutical composition is a therapeutically effective amount. In this connection the peptides contained in the composition can bind to at least two different HLA-types.

The present invention relates, as a further object of the invention to nucleic acid molecules encoding the peptides with sequence ID Nos. 1 to 79.

The nucleic acid molecules can represent DNA- or RNA-molecules and can be used for immune therapy of cancer as well. Thereby the peptide expressed by the nucleic acid molecule induces an immune response against tumor cells, which express the peptide.

According to the invention the nucleic acid molecules can be provided in a vector.

The invention further relates to a cell genetically modified by means of the nucleic acid molecule so that the cell is producing a peptide having sequence ID Nos. 1 to 79.

For this purpose, the cells are transfected with DNA or corresponding RNA encoding the peptides, thereby expressing the peptides on the cells. For this purpose, for example dendritic cells, monocytes or B-lymphocytes are suitable as antigen-presenting cells.

It will be understood that the features which are mentioned above and the features still to be explained below can be used not only in the combinations which are in each case specified but also in other combinations or on their own without departing from the scope of the present invention.

Embodiments of the invention are displayed and explained in the figures below.

MODES OF CARRYING OUT THE INVENTION

Example 1

1.1 Patient Samples

Figure 1:
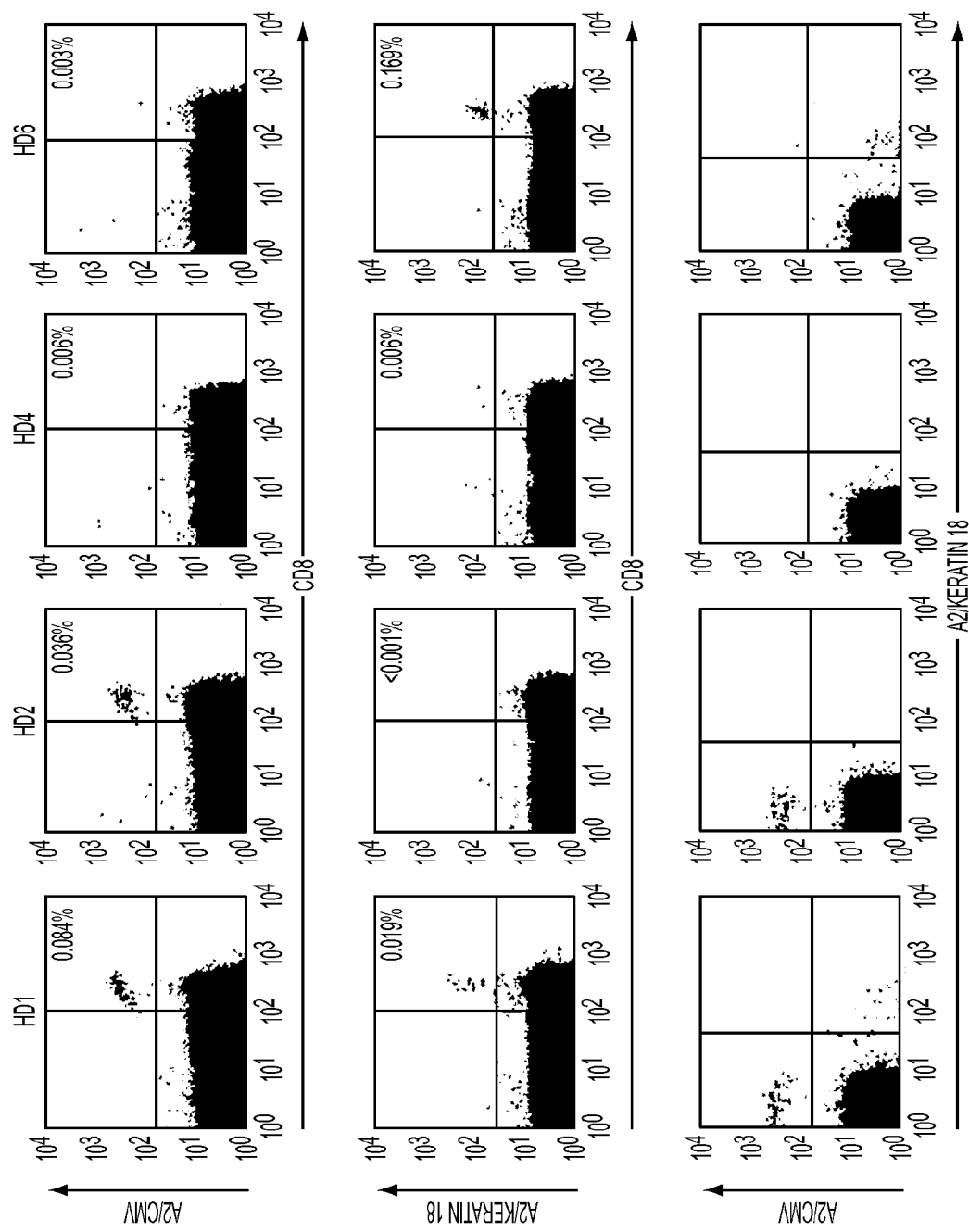
FIG. 1 shows the detection of CD8+-T-lymphocytes specific for keratin 18.

Samples of patients having histologically confirmed renal cell carcinoma were obtained from the department of urology, University of Tubingen. Both patients had not received preoperative therapy. Patient No. 1 (in the following designated RCC01) had the following HLA-typing: HLA-A*02 A*68 B*18 B*44; patient No. 2 (in the following designated RCC13) HLA-A*02 A*24 B*07 B*40.

1.2 Isolation of MHC-Class-1-Bound Peptides

Shock-frozen tumor samples were processed as described in Schirle, M. et al., Identification of tumor-associated MHC-class I ligands by a novel T cell-independent approach, 2000, European Journal of Immunology, 30: 2216-2225. Peptides were isolated according to standard protocols using monoclonal antibody W6/32 being specific for HLA class I or monoclonal antibody BB7.2 being specific for HLA-A2. Production and utilization of these antibodies is described by Barnstable, C. J. et al., Production of monoclonal antibodies to group A erythrocytes, HLA and other human cell surface antigens—New tools for genetic analysis, 1978, Cell, 14:9-20 and Parham, P. & Brodsky, F. M., Partial purification and some properties of BB7.2. A cytotoxic monoclonal antibody with specificity for HLA-A2 and a variant of HLA-A28, 1981, Hum. Immunol., 3:277-299.

1.3 Mass Spectrometry

Peptides from tumor tissue of patient RCC01 were separated by reversed phase HPLC(SMART-system, μRPC C2/C18 SC 2.1/19, Amersham Pharmacia Biotech) and fractions were analyzed by nanoESI MS. In doing so it was proceeded as described in Schirle, M. et al., Identification of tumor-associated MHC class I ligands by a novel T cell-independent approach, 2000, European Journal of Immunology, 30: 2216-2225.

Peptides from tumor tissue of patient RCC13 were identified by online capillary LC-MS as mentioned above with minor modifications: Sample volumes of about 100 μl were loaded, desalted and preconcentrated on a 300 μm*5 mm C18 μ-precolumn (LC packings). A syringe pump (PHD 2000, Harvard Apparatus, Inc.) equipped with a gastight 100 μl-syringe (1710 RNR, Hamilton), delivered solvent and sample at 2 μl/min. For peptide separation, the preconcentration column was switched in line with a 75 μm*250 mm C-18-column (LC packings). Subsequently a binary gradient of 25%-60% B within 70 min was performed, applying a 12 μl/min flow rate reduced to approximately 300 nl/min with a precolumn using a TEE-piece (ZT1C, Valco) and a 300 μm*150 mm C-18-column.

A blank run was always included to ensure that the system was free of residual peptides. On-line fragmentation was performed as described and fragment spectra were analyzed manually. Database searches (NCBInr, EST) were made using MASCOT.

1.4 Identification of 77 MHC-Class-I-Ligands of Tumorous Tissue of Patient RCC01

In the enclosed Table 1 the ligands are listed which were bound to HLA-A*02, HLA-A*68, HLA-B*18 or HLA-B*44. Peptides that bound to HLA-A*02 reflected the allele-specific peptide motif: On position 2 Leucine, Valine, Isoleucine, Alanine or Methionine and at the C-terminus Leucine, Valine, Isoleucine or Alanine. Most ligands were derived from so-called housekeeping proteins but ligands from proteins with reported tumor-associated associations could be detected also.

HLA-A*68 ligands were identified by their anchor amino acid Threonine, Isoleucine, Valine, Alanine or Leucine on position 2 and Arginine or Lysine at the C-terminus. This indicated to subtype HLA-A*6801. Two other ligands from adipophilin were found among HLA-A*68 presented peptide, MTSALPEIQK and MAGDIYSVFR, and further ETIPLTAEKL deriving from tumor-associated cycline D1. Peptide TIVNILTNR derives from Annexin II, this protein proved as immunogenic in connection with MHC-class-II in melanoma patients (see Heinzel et al., The self peptide annexin II (208-223) presented by dendritic cells sentsizes autologous CD4+ T-lymphocytes to recognize melanoma cells, 2001, Cancer Immunol. Immunother. 49: 671-678). Further ligands were carrying glutamic acid on position 2 which is an anchor amino acid of the HLA-B*44-subtype. Since the peptide motif of HLA-B*18 is unknown the distinction between ligands of these two HLA-B-molecules was not possible.

1.5 MHC-Class-I-Ligands of Tumorous Tissue of Patient RCC13

With this tumorous tissue, too, the same ligands could be identified, which have been identified in patient RCC01 and which derived from met-protooncogene (c-Met) and keratin 18: peptides having sequence ID Nos. 1 and 3. In addition, further ligands could be obtained from this tumorous tissue: A ligand could be identified which derives from nicotinamide-N-methyltransferase (NNMT); this gene is overexpressed in more than 95% of all renal carcinoma. Further, some other ligands overlap with the peptide repertoire of RCC01.

1.6 Detection of Keratin 18-Specific T-Cells in Normal CD8-T-Cell Repertoire Peripheral blood mononuclear cells from healthy patients were stained with HLA-A*0201-tetramers which were folded with adipophilin-, keratin 18- or met-protooncogene (c-Met)-peptides: For generation of the tetramers, recombinant HLA-A*0201-molecules were folded in vitro with the peptides SVASTITGV (SEQ ID No. 2, adipophilin), ALLNIKVKL (SEQ ID No. 3, keratin 18) or YVDPVITSI (SEQ ID No. 1, met-protooncogene, c-Met), purified by means of gel filtration, biotinylated and mixed with streptavidin to link the monomers.

Unexpectedly, a significant population of $CD8^+$-T-lymphocytes specific for keratin 18 was found in four out of 22 healthy individuals. In FIG. 1, the results of double staining are shown in dotplots, whereby in the middle row the results of staining with keratin 18 is shown. Between 0.02 and 0.2% of the $CD8^+$-positive T-cells were specific for keratin 18. As can be seen from the lower row of the dotplots, binding of the keratin 18-tetramer was specific.

Example 2

To analyze presentation of the peptides with SEQ ID No. 1 (YVDPVITSI) (peptide fragment of c-Met-protooncogene) and SEQ ID No. 2 (peptide fragment of adipophilin) by tumor cells and their recognition by CTL, CTL were induced in vitro, which were specific for the c-Met-peptide (peptide with SEQ ID No. 1) and CTL which were specific for the adipophilin-peptide (SEQ ID No. 2). In doing so, dendritic cells (DC) derived from healthy HLA-A*02-positive donors were used.

2.1 Generation of DC

Peripheral blood mononuclear cells (PBMNC) were isolated by Ficoll/Paque-(Biochrom, Berlin, Germany)-density gradients centrifugation of heparinized blood obtained from buffy coat preparations of healthy volunteers from the blood bank of the University of Tübingen. Cells were seeded ($1\times10^7$ cells/3 ml per well) into 6-well plates (Falcon, Heidelberg, Germany) in RP10 media (RPMI 1640, supplied with 10% heat-inactivated fetal calf serum and with antibiotics). After 2 hours of incubation at 37° C. and 5% $CO_2$, non-adherent cells were removed and the adherent blood monocytes were cultured in RP10 medium supplemented with the following cytokins: human recombinant GM-CSF (granulocyte makrophage colony stimulating factor; Leukomax, Novartis; 100 ng/ml), Interleukin IL-4 (R&D Systems, Wiesbaden, Germany, 1000 IU/ml) and TNF-α (tumor necrosis factor α) (R&D Systems, Wiesbaden, Germany, 10 ng/ml).

2.2 Synthesis of Peptides

Exemplary, two HLA-A*02-binding peptides (c-Met SEQ ID No. 1, YVDPVITSI) or adipophilin (SEQ ID No. 2, SVASTITGV) which were identified as described above) were synthesized using standard F-moc chemistry on a peptide synthesizer (432A, Applied Biosystems, Weiterstadt, Germany) and analyzed by reversed phase HPLC and mass spectrometry. In that way, sufficient amounts of the identified peptides can be generated.

2.3 Induction of Antigen-Specific CTL-Response Using HLA-A*02 Restricted Synthetic Peptides For CTL induction, the DC obtained in step 2.1 ($5\times10^5$) were pulsed with the peptides obtained in step 2.2 with SEQ ID No. 1 or SEQ ID No. 2, each with 50 µg/ml for 2 hours, washed and incubated with $2.5\times10^6$ autologous PBMNC in RP10 medium.

After 7 days of culture, cells were restimulated with autologous PBMNC pulsed with peptides. In doing so, 1 ng/ml human recombinant Interleukin IL-2 (R&D Systems) was added on days 1, 3 and 5. The cytolytic activity of thereby induced CTL was analyzed on day 5 after the last restimulation in a standard $^{51}$Cr-release-assay (see below, under 2.4: CTL-assay).

2.4 CTL-Assay

In the CTL-assays, tumor cells, peptide-pulsed cells of different cell lines and autologous DC were used as target cells. Peptide-pulsed cells were pulsed with 50 µg/ml peptide (SEQ ID No. 1 or SEQ ID No. 2) for 2 hours. All target cells were labeled with [$^{51}$Cr] sodium chromate in RP10 (RPMI 1640, supplemented with 10% heat inactivated calf serum and antibiotics) for 1 hour at 37° C. Subsequently, $10^4$ cells/well were transferred to a 96-well round bottomed plate. Varying numbers of CTL were added to give a final volume of 200 µl and incubated for 4 hours at 37° C. At the end of the assays, supernatants (50 µl/well) were harvested and counted in a beta-plate counter. The percent-specific lysis was calculated as: 100×(experimental release-spontaneous release/maximal release-spontaneous release). The spontaneous and maximal release were determined in the presence of either medium or 2% Triton X-100, respectively.

2.5 Results of the CTL-Induction a) CTL-Cytotoxic Activity Against Peptide-Pulsed Dc In FIG. 2, the results of the $^{51}$Cr-release-assay (see under 2.4) with respect to the cytotoxic activity of induced CTL (see under 2.3) against T2- or DC-cells is shown. The T2-cell line is HLA-A*02-positive and TAP (transporter associated with antigen processing) deficient; (TAP-peptide-transporter transport peptide fragments of a proteinous antigen from the cytosol to the endoplasmatic reticulum, where they associate with MHC-molecules).

Figure 2A:
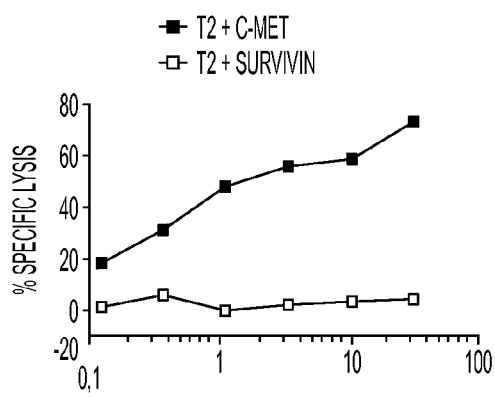
FIGS. 2a-d show the induction of CTL-responses in vitro, specific for the c-Met-peptide (SEQ ID No. 1), FIGS. 2a and 2b, or the adipophilin-peptide (SEQ ID No. 2), FIGS. 2c and 2d.
Figure 2B:
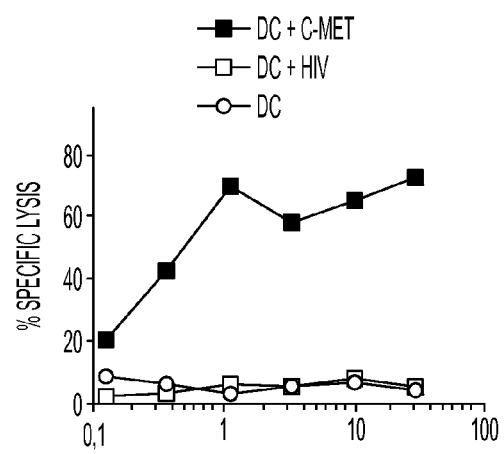
Figure 2C:
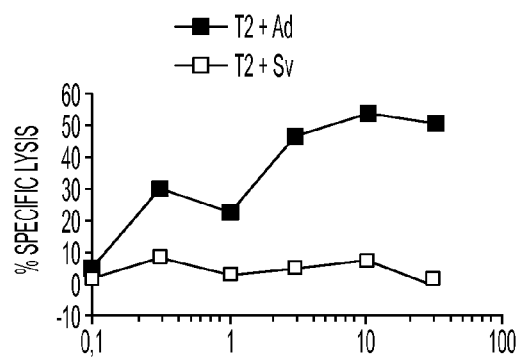
Figure 2D:
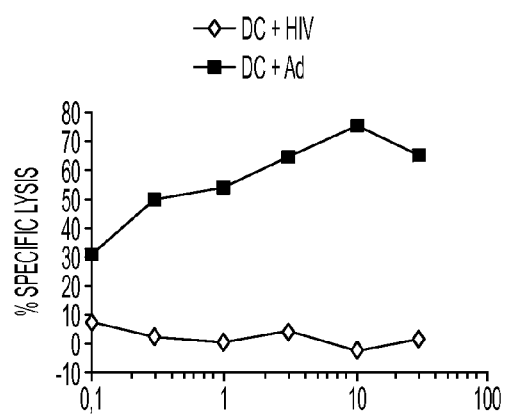

In FIGS. 2a and 2b, the cytotoxic activity of CTL induced with peptide with SEQ ID NO:1 against T2-cells and DC is shown, both cell types had previously been pulsed with the (c-Met-)peptide with SEQ ID No. 1 (black filled boxes) or an ir-relevant peptide (Survivin "Sv"; ELTLGEFLKL; SEQ ID No. 80) or HIV (ILKEPVHGV; Pol. HIV-1 reverse transcriptase peptide, position 476-484; SEQ ID No. 81). In FIGS. 2c and 2d, the cytotoxic activity of CTL induced with peptide with SEQ ID NO:2 against T2- and DC-cells is shown, which had previously been pulsed with the (adipophilin)-peptide with the SEQ ID No. 2.

The specific lysis, which is demonstrated in the release of $^{51}$Cr, is, in FIGS. 2a-2d,—as well as in the CTL-lysis-diagrams of FIGS. 3-5—shown vs. different ratios of effector cells (CTL) to target cells ($^{51}$Cr-labeled cells to be lysed).

As can be seen from FIGS. 2a-2d, an antigen-specific killing of cells could be demonstrated with a CTL-cell line, which has been generated after 2-weekly restimulation: Only cells were lysed by an increasing amount of CTL, which presented either the c-Met-peptide with the SEQ ID No. 1 (FIGS. 2a and 2b) or the adipophilin-peptide with the SEQ ID NO:2 (FIGS. 2c and 2d) (see in the FIGS. 2a-2d curves with black filled boxes, respectively); while control cells pulsed with irrelevant peptides were not lysed (curves with empty boxes). Thereby the specificity of the cytolytic activity could be demonstrated.

b) CTL-Cytotoxic Activity Against Tumor Cell Lines

Next, it was tested, in a standard tumor $^{51}$Cr-release-assays again, whether CTL specific for the c-Met-peptide with SEQ ID No. 1 or for adipophilin-peptide with SEQ ID No. 2 recognized and lysed tumor cells, which endogeously express the c-Met-protooncogene or adipophilin.

In doing so, the following cell lines, $^{51}$Cr-labeled, HLA-A*02-positive, were used: HCT 116 (colon cancer; obtained from Prof. G. Pawelec, Tubingen, Germany), A 498, MZ 1257 and MZ 1774 (renal cell carcinoma; obtained from Prof. A. Knuth, Frankfurt, Germany), MCF-7 (breast cancer; obtained from ATCC, American Type Culture Collection), Mel 1479 (Malignant melanoma; obtained from Prof. G. Pawelec, Tübingen, Germany) and U 266 (multiple myeloma; obtained from Prof. G. Pawelec, Tübingen, Germany). These cell lines express c-Met-protooncogene and adipophilin as target structures ("targets").

In the experiments CEBV (Epstein-Barr-virus)-immortalized B-cell line Croft, HLA-A*01-positive; obtained from O.J. Finn, Pittsburgh, USA) and cell line SK-OV-3 (ovarian cancer; HLA-A*03-positive; obtained from O.J. Finn, Pittsburgh, USA) were used as negative controls. K 562-cells (for example obtainable at the German Collection of Mikro Organisms and Cell Cultures DSMZ; ACC 10) were used to determine the activity of natural killer cells (NK) since the cell line is highly sensitive for these killer cells.

All cell lines were cultivated in RP10 medium (RPMI 1640, supplemented with 10% heat-inactivated fetal calf serum and antibiotics).

With the above-mentioned tumor cell lines and the CTL induced $^{51}$Cr-release assays (see under 2.4.) were carried out as mentioned above.

Figure 3A:
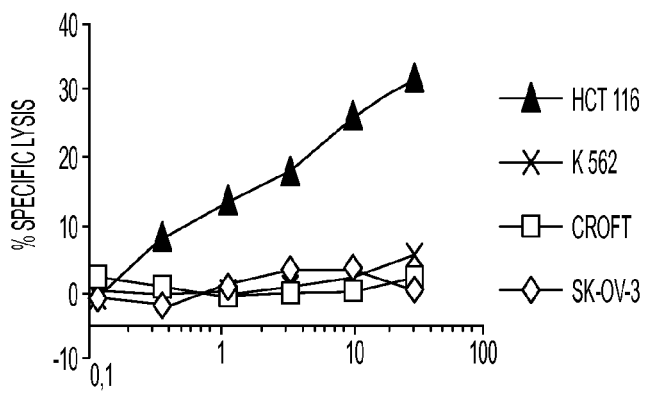
FIGS. 3a-f show antigen-specific lysis of tumor cell lines expressing c-Met or adipophilin, mediated by c-Met-peptide (SEQ ID No. 1), FIGS. 3a-d, or adipophilin-peptide (SEQ ID No. 2), FIGS. 3e and 3f, induced CTL.
Figure 3B:
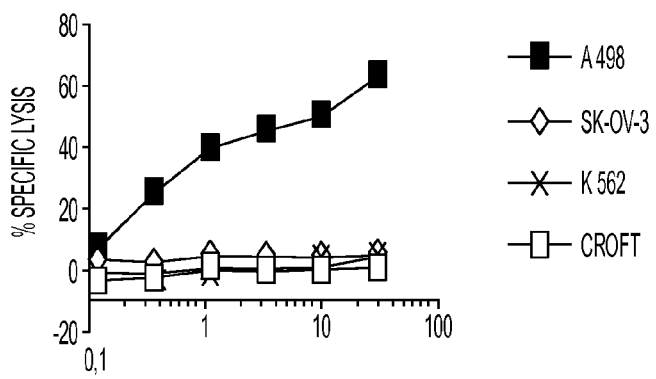
Figure 3C:
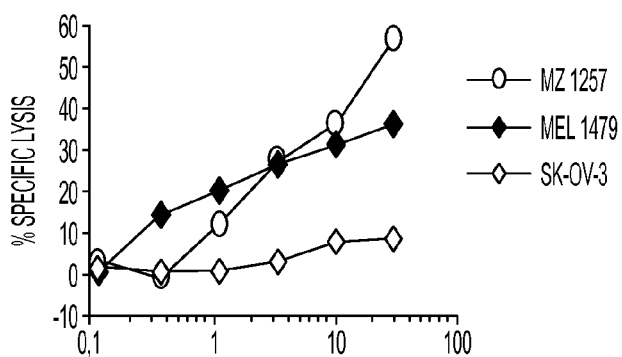
Figure 3D:
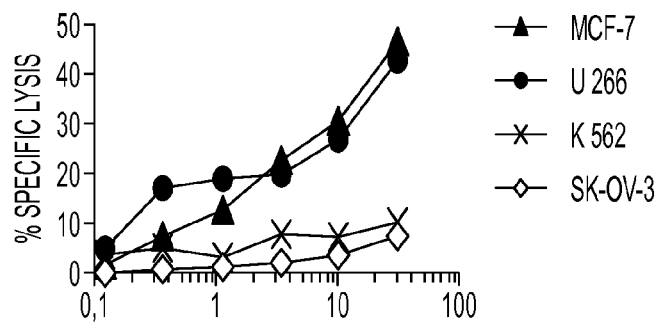
Figure 3E:
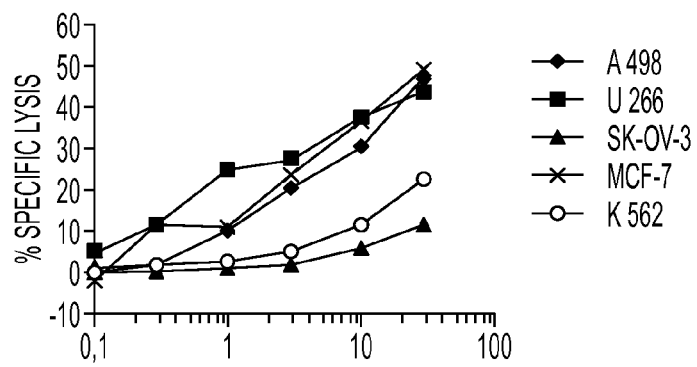
Figure 3F:
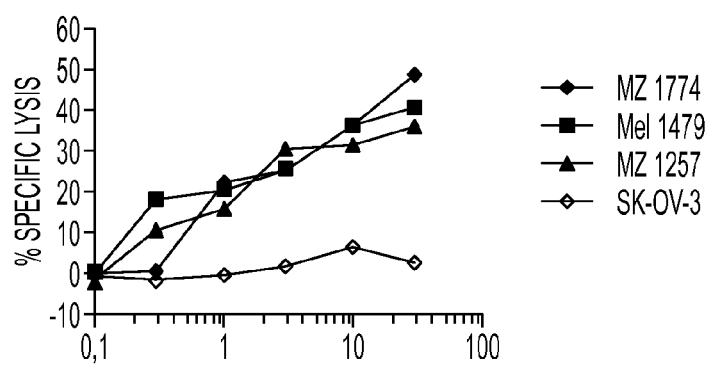

FIGS. 3a-3f show the results of these CTL-assays, whereby in FIGS. 3a-3d CTL were used which were induced using c-Met-peptide with SEQ ID No. 1, and in FIGS. 3e-3f CTL were used, which were induced using adipophilin peptide with SEQ ID No. 2.

As can be seen from FIGS. 3a-3f, the CTL specific for c-Met-peptide with SEQ ID No. 1 (FIGS. 3a-3d) or specific for adipophilin peptide with SEQ ID No. 2 (FIGS. 3e and 3f) were able to efficiently lyse tumor cells expressing both HLA-A*02 and c-Met or adipophilin (that is in FIG. 3a cell line HCT 116, in FIG. 3b cell line A 498, in FIG. 3c cell lines MZ 1257 and MEL 1479 and in FIG. 3d cell lines MCF-7 and U 266; in FIG. 3e cell lines A 494, U 266 and MCF-7, in FIG. 3f cell lines MZ 1774, Mel 1479 and MZ 1257). Specific lysis was measured—as mentioned under 2.4.—via $^{51}$Cr release. There was no lysis of the control cell line SK-OV-3 (HLA-A-*02-negative), neither through CTL, which were induced by the peptide with SEQ ID NO:1 nor through CTL, which were induced by the peptide with SEQ ID NO:2. Thus, it could be demonstrated that both peptides have to be presented on tumor cells in connection with HLA-A*02-molecules to efficiently lyse the target cells. Further, the antigen-specificity and the MHC-restriction of the CTL is proved in that way.

CTL-cells induced in vitro with the peptide having SEQ ID NO:1 did not recognize the $K_{562}$ cell line (see FIGS. 3a, 3b and 3d), indicating that the cytotoxic activity was not mediated by natural killer (NK)-cells.

c) Inhibition-Assays

To further verify the antigen-specificity and the MHC-restriction of the in-vitro-induced CTL, inhibition assays with non-$^{51}$Cr-labeled ("cold") inhibitor cell lines were performed.

In doing so, the ability of peptide-pulsed cell lines was analyzed to inhibit the lysis of tumor cells (competition assay). For this purpose, an excess of inhibitor (that is an excess of unlabeled pulsed cells) was used. The ratio of inhibitor (peptide-pulsed cells) to target (tumor cells) was 20:1. When inhibitor cell lines were lysed, no $^{51}$Cr was released, since the inhibitor cell lines were unlabeled.

Cell line T2 (HLA-A*02; TAP-deficient; see under 2.5.a) was used as inhibitor. Previous to the assay, this cell line T2 was pulsed with the relevant peptides (SEQ ID NOS:1 or 2) or an irrelevant control peptide (Survivin Sv), SEQ ID NO:80), respectively.

Figure 4A:
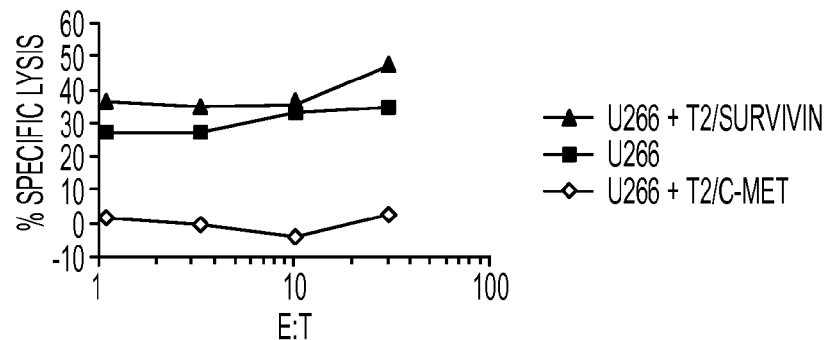
FIGS. 4a-c show lysis-inhibition assays with 51 Cr-labeled tumor cells and unlabeled pulsed T2-cells mediated by c-Met-peptide (SEQ ID No. 1), FIGS. 4a and 4b, or adipophilin-peptide (SEQ ID No. 2), FIG. 4c) induced CTL.
Figure 4B:
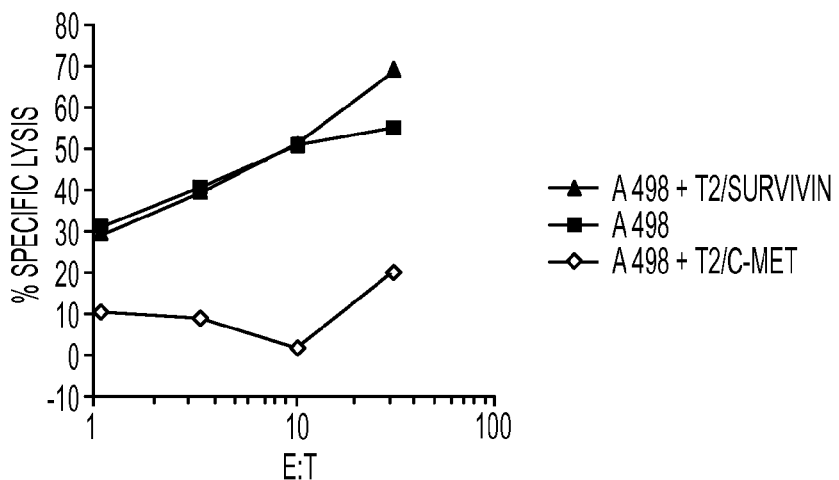
Figure 4C:
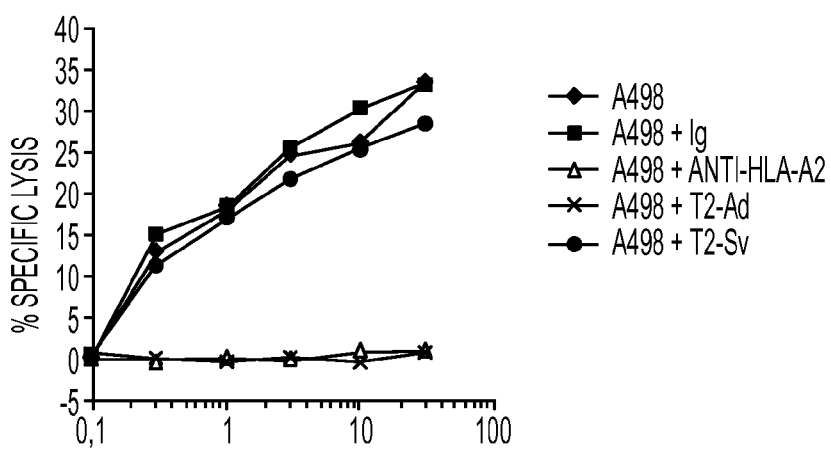

Results of these tests are shown in FIGS. 4a-4c, whereby in FIGS. 4a and 4b CTL were used which were c-Met-peptide-induced (SEQ ID NO:1) and in FIG. 4c CTL were used, which were adipophilin-peptide-induced (SEQ ID NO:2).

In FIGS. 4a and 4b, lysis of the $^{51}$Cr-labeled cell lines U 266 and A 498 was tested without inhibitor cell line (see the curve with black filled boxes); lysis with inhibitor cell line T2, pulsed with an irrelevant peptide (Survivin; SEQ ID NO:80; negative control, curves with the filled triangles); and lyses with the inhibitor cell line T2 pulsed with the c-Met-peptide with SEQ ID NO:1 (curves with the empty rhombus).

Without inhibitor cells, lysis of tumor cells by CTL could be demonstrated (see in FIGS. 4a-4d curves with black filled boxes, respectively). Further, as can be seen from FIGS. 4a and 4b, when using an excess of inhibitor target tumor cells were not lysed (and no $^{51}$Cr was released), if the inhibitor target was pulsed with c-Met-peptide with SEQ ID NO:1 (see curves with the empty rhombus symbols, respectively). The activity of the CTL was directed against the excess unlabeled T-cells, so that these cells and not the tumor cells were lysed. The T2-cells pulsed with an irrelevant peptide (Survivin respectively; SEQ ID NO:80) were not able to inhibit the lysis of tumor cells by CTL, so that released $^{51}$Cr could be measured (see in FIGS. 4a and 4b curves with black filled triangles).

A similar event could be shown when using CTL induced with adipophilin peptide with SEQ ID NO:2 (see FIG. 4c):

MHC-restriction and antigen-specificity of the cytotoxic activity of the adipophiline-induced CTL could be demonstrated by using a HLA-A*02-specific monoclonal antibody and in an inhibition assay with unlabeled ("cold") inhibitor: The results of this experiment are shown in FIG. 4c. A 498-tumor cells were blocked when adding HLA-A*02-specific antibody (monoclonal antibody BB7.2, IgG2b, obtained from S. Stefanovic, Tubingen) so that they were not lysed by the added CTL and no $^{51}$Cr was released (see FIG. 4c curve with filled triangle-symbols). As a control a non-specific antibody was used, which did not block the HLA-A*02-molecule (ChromPure Maus IgG, Dianova, Germany; see in FIG. 4c curve with filled boxes). With these inhibition assays, the cells were incubated with 10 µg/ml antibody previous to seeding on the 96-well-plates for 30 min.

Further, it could be demonstrated that the T2-competition cell line pulsed with the irrelevant peptide Survivin (SEQ ID NO:80) (T2/SV), was not able to inhibit CTL-induced lysis of tumor cell line A 498 (see in FIG. 4c curve with black filled circles), but T2-inhibitor cell line pulsed with adipophilin peptide with SEQ ID NO:2 (T2/AD) was able to inhibit the lysis of the tumor cell line, so that—refrain to the latter case—no $^{51}$Cr release could be measured (see in FIG. 4c curve with x-symbols).

d) Specific Lysis of Transfected DC

In a next experiment, the cytotoxic activity of CTL in an autologous setting was analyzed. In doing so, autologous DC, generated from the same PBMNC that were utilized for CTL induction (see under 2.2.), were used as target cells. Prior to the CTL-assay, the DC were electroporated with RNA, which was previously isolated either from tumor cell lines or which represented control-RNA (in vitro transcribed EGFP—RNA, enhanced Green fluorescent protein-RNA); plasmide: pSP64 Poly(A) EGFPII, obtained from Van Tendeloo, Antwerp, Belgium). Total RNA of tumor cells was isolated with the QIAGEN Rneasy Mini Kit (QIAGEN, Hilden, Germany) according to the manufacturer's protocol. Quantity and purity of RNA were determined by spectrophotometry and stored in aliquots at −80° C.

Prior to electroporation on day 6, immature DC were washed twice with serum-free X-VIVO 20 medium (Bio-Whittaker, Walkersville, USA) and resuspended to a final concentration of $2 \times 10^7$ cells/ml. Subsequently, 200 µl of the cell suspension were mixed with 10 µg of total RNA and electroporated in a 4 mm-cuvette using an Easyject Plus™ (Peglab, Erlangen, Germany) (parameters: 300 V, 150 µF, 1540Ω, pulse time 231 ms). After electroporation the cells were immediately transferred into RP10 medium and returned to the incubator. More than 80% of the cells proved to be viable after electroporation.

Figure 5A:
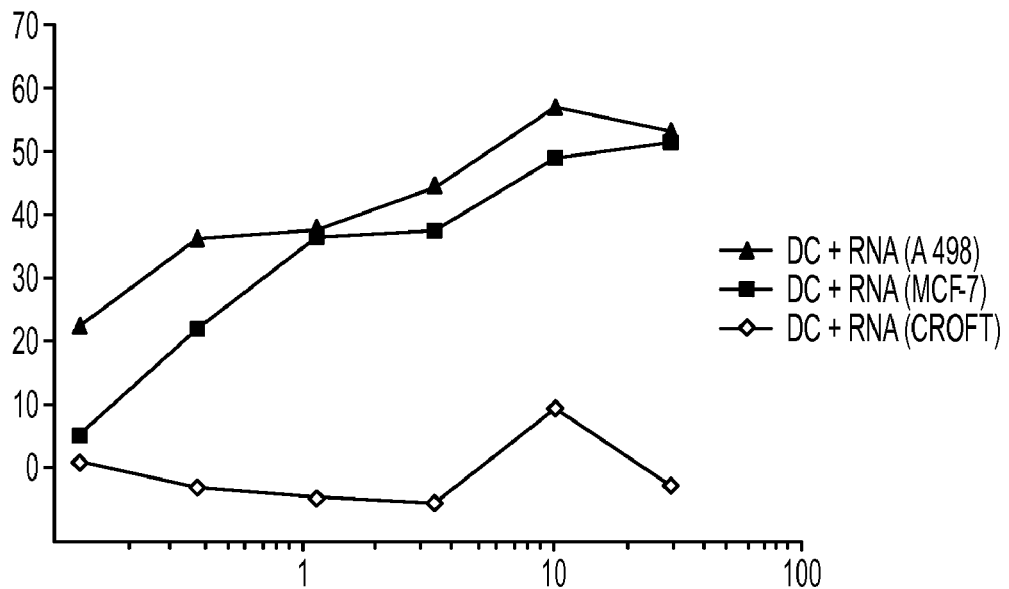
FIGS. 5a and b show lysis of autologous dendritic cell transfected with tumor RNA mediated by c-Met-peptide (SEQ ID No. 1), FIG. 5a, or adipophilin-peptide (SEQ ID No. 2), FIG. 5b, induced CTL.
Figure 5B:
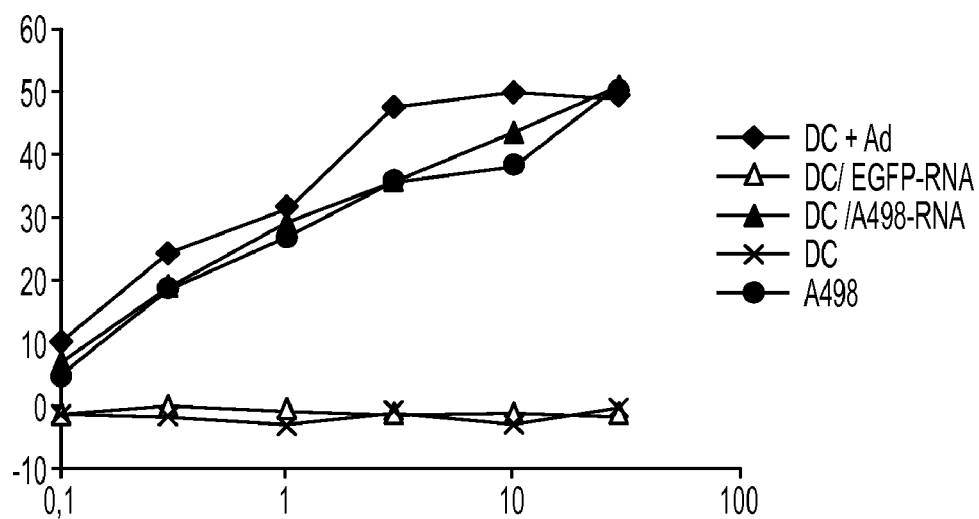

The results of these experiments are shown in FIGS. 5a and 5b. In FIG. 5a CTL were used, which were induced with c-Met-peptide with SEQ ID NO: 1, in FIG. 5b CTL were used which were induced with adipophilin peptide with SEQ ID NO:2.

After performing the CTL-assay with the CTL induced by c-Met-peptide (SEQ ID NO: 1) (see under 2.4.) a specific lysis of DC could be demonstrated which were electroporated with RNA of c-Met-expressing tumor cell lines (A 498 and MCF-7) (see in FIG. 5a, curves with black filled symbols). DC electroporated with RNA of the non-C-met-expressing tumor cell line Croft were not lysed (see curve with the empty rhombus).

CTL induced with adipophilin-peptide with SEQ ID NO:2 lysed DC which were electroporated with RNA of the adipophilin-expressing cell line A 498 (see in FIG. 5b curve with black filled triangles). Further, DC were lysed which were pulsed with the adipophilin-peptide SEQ ID NO:2 (see in FIG. 5b curve with black filled rhombus). On the other hand, DC electroporated with control (EGFP) RNA were not lysed (see in FIG. 5b curve with the empty triangles).

Thus it could be demonstrated that—after transfection of the DC with RNA of c-Met- or adipophilin-positive tumor cells—the identified peptides, that is c-Met-peptide with SEQ ID NO: 1 and adipophilin-peptide with SEQ ID NO:2, were processed and presented.

e) Induction of Adipophilin-Specific CTL in a Patient with Chronic Lymphatic Leukemia In a further experiment, CTL were generated from PBMNC of HLA-A*0201-positive patient with chronic lymphatic leukemia (CLL), which were specific for adipophilin-peptide with SEQ ID NO:2. The patient was in remission after treatment with fludarabine. Further, autologous CLL-cells and DC of this patient were used as $^{51}$Cr-labeled targets in an assay, in which $^{51}$Cr-release is mediated by the peptide-induced CTL.

Figure 6:
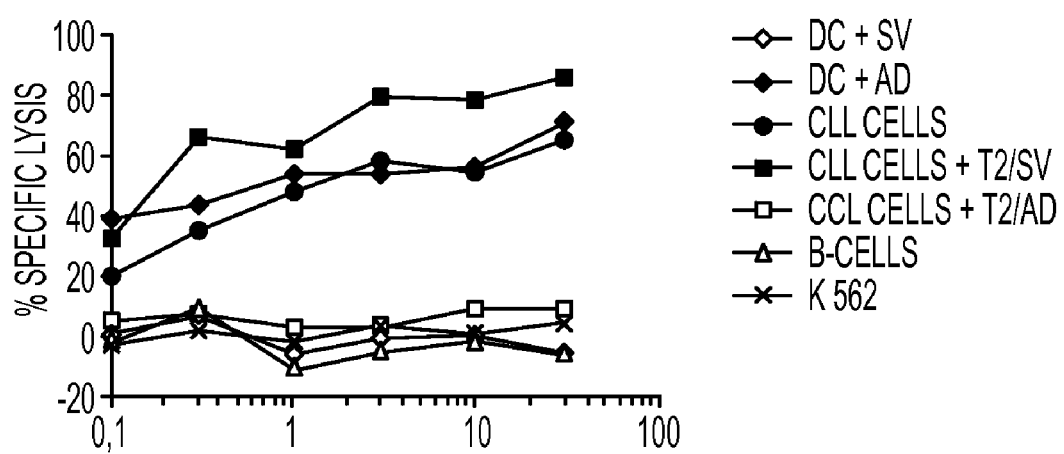
FIG. 6 shows that adipophilin-specific autologous CTL induced in vitro recognize autologous tumor cells of a patient with chronic lymphatic leukaemia but not autologous dendritic or B-cells.

As shown in FIG. 6, the peptide-induced CTL efficiently lysed autologous DC from this patient that were pulsed with the adipophilin peptide with SEQ ID NO:2 ("DC+AD") as well as the autologous CLL-cells ("CLL cells"). DC which were pulsed with the irrelevant peptide Survivin with SEQ ID NO:80 were—on the other hand—not lysed ("DC+SV"). Also, non-malignant B-cells and cell line K 562 were not lysed by CTL.

The specificity of the CTL-response was further confirmed in a target inhibition assay, using the cell line T2 (see above) as inhibitor cells, which were pulsed with the adipophilin peptide with SEQ ID NO:2 or with the irrelevant peptide Survivin with SEQ ID NO:80, respectively. The CTL induced with adipophilin-peptide with SEQ ID NO:2 lysed the excess inhibitor cell lines which were pulsed with the relevant peptide with SEQ ID NO:2 no that $^{51}$Cr-labeled tumor cells were not lysed in this case (see in FIG. 6 the curve with empty boxes).

In conclusion, the inventors could show that the identified peptides represent promising substances in the scope of an immune therapy for many (tumor) diseases.

TABLE 1

| Sequence | Position/Gene | Acc. No. | SEQ ID-No. |
|---|---|---|---|
| Patient RCC01 HLA-A*02 | | | |
| 1. YVDPVITSI | 654-662 met proto-oncogen | J02958 | SEQ ID-Nr. 1 |
| 2. SVASTITGV | 129-137 adipose differentiation-related protein | X97324 | SEQ ID-Nr. 2 |
| 3. ALLNIKVKL | 365-373 keratin 18 | M26326 | SEQ ID-Nr. 3 |
| 4. ALFDGDPHL | 1-9 KIAA0367 | AB002365 | SEQ ID-Nr. 4 |

TABLE 1-continued

| Sequence | Position/Gene | Acc. No. | SEQ ID-No. |
|---|---|---|---|
| 5. RLLDYVVNI | 679-687<br>hypothetical protein FLJ20004 | AB040951 | SEQ ID-Nr. 5 |
| 6. ALANGIEEV | 101-109<br>apolipoprotein L, 3 | AY014906 | SEQ ID-Nr. 6 |
| 7. QLIDKVWQL | 593-601<br>SEC14 (S. cerevisiae)-like 1 | D67029 | SEQ ID-Nr. 7 |
| 8. ALSDLEITL | 389-397<br>mitogen inducible 2 | Z24725 | SEQ ID-Nr. 8 |
| 9. ILDTGTIQL | 174-182<br>kidney-and liver-specific gene | AB013094 | SEQ ID-Nr. 9 |
| 10. SLLGGDVVSV | 27-36<br>delta sleep inducing peptide, immunoreactor | AF153603 | SEQ ID-Nr. 10 |
| 11. FLDGNELTL | 167-175<br>chloride intracellular channel 1 | U93205 | SEQ ID-Nr. 11 |
| 12. NLLPKLHIV | 179-187<br>chloride intracellular channel 1 | U93205 | SEQ ID-Nr. 12 |
| 13. ALASHLIEA | 507-515<br>EH-domain containing 2 | AF181263 | SEQ ID-Nr. 13 |
| 14. SLYGGTITI | 296-304<br>hypothetical protein FLJ11189 | AK000697 | SEQ ID-Nr. 14 |
| 15. FLLDKKIGV | 218-226<br>chaperonin containing TCP1, subunit 2 (beta) | AF026166 | SEQ ID-Nr. 15 |
| 16. FLDGNEMTL | 178-186<br>chloride intracellular channel 4 | AF097330 | SEQ ID-Nr. 16 |
| 17. AIVDKVPSV | 147-155<br>coat-protein gamma-cop | AF100756 | SEQ ID-Nr. 17 |
| 18. DVASVIVTKL | 241-250<br>signal recognition particle 54 kD | U51920 | SEQ ID-Nr. 18 |
| 19. LASVSTVL | 130-137<br>hemoglobin, alpha 2 | AF230076 | SEQ ID-Nr. 19 |
| 20. VMAPRTLVL | 3-11<br>HLA-A |  | SEQ ID-Nr. 20 |
| 21. LLFDRPMHV | 267-275<br>hnRNP M | L03532 | SEQ ID-Nr. 21 |
| HLA-A*68 |  |  |  |
| 22. MTSALPIIQK | 62-71<br>adipose differentiation-related protein | X97324 | SEQ ID-Nr. 22 |
| 23. MAGDIYSVFR | 349-358<br>adipose differentiation-related protein | X97324 | SEQ ID-Nr. 23 |
| 24. ETIPLTAEKL | 115-124<br>cyclin D1/PRADI | X59798 | SEQ ID-Nr. 24 |
| 25. DVMVGPFKLR | 934-943<br>A kinase (PRKA) anchor protein 2 | AJ303079 | SEQ ID-Nr. 25 |
| 26. THDILTKR | 64-72<br>annexin A1 | X05908 | SEQ ID-Nr. 26 |
| 27. TIVNILTNR | 55-63<br>annexin A2 | BC001388 | SEQ ID-Nix 27 |
| 28. TIIDIITHR | 385-393<br>annexin A6 | J03578 | SEQ ID-Nr. 28 |
| 29. SIFDGRVVAK | 107-116<br>putative membrane protein | AB020980 | SEQ ID-Nr. 29 |

TABLE 1-continued

| Sequence | Position/Gene | Acc. No. | SEQ ID-No. |
|---|---|---|---|
| 30. STIEYVIQR | 115-123<br>Sec23 (*S. cerevisiae*) homolog B | BC005032 | SEQ ID-Nr. 30 |
| 31. ELIKPPTILR | 132-141<br>adaptor-related protein complex 3 | AF092092 | SEQ ID-Nr. 31 |
| 32. EIAMATVTALR | 248-258<br>aldolase A, fructose-biphosphate | X12447 | SEQ ID-Nr. 32 |
| 33. ETIGEILKK | 95-103<br>hnRNP K | BC000355 | SEQ ID-Nr. 33 |
| 34. SLADIMAKR | 86-94<br>ribosomal protein L24 | BC000690 | SEQ ID-Nr. 34 |
| HLA-B*44 oder HLA-B*18 | | | |
| 35. EEIAFLKKL | 229-237<br>vimentin | M14144 | SEQ ID-Nr. 35 |
| 36. DEAAFLERL | 92-100<br>caldesmon 1 | M64110 | SEQ ID-Nr. 36 |
| 37. DEMKVLVL | 545-552<br>spectrin, beta, non-erythrocytic 1 | M96803 | SEQ ID-Nr. 37 |
| 38. DEVKFLTV | 191-198<br>annexin A4 | M82809 | SEQ ID-Nr. 38 |
| 39. NENSLFKSL | 935-943<br>clathrin, heavy polypeptide (Hc) | D21260 | SEQ ID-Nr. 39 |
| 40. DEFKVVVV | 373-380<br>coat protein, gamma-cop | AF100756 | SEQ ID-Nr. 40 |
| 41. EEVKLIKKM | 137-145<br>ferritin, light polypeptide | M11147 | SEQ ID-Nr. 41 |
| 42. DEVKLPAKL | 158-166<br>polymerase I and transcript release factor | AF312393 | SEQ ID-Nr. 42 |
| 43. TERELKVAY | 637-645<br>hypothetical protein FLJ20004 | AB040951 | SEQ ID-Nr. 43 |
| 44. NEFSLKGVDF | 86-95<br>ets-1 | J04101 | SEQ ID-Nr. 44 |
| 45. NEQDLGIQY | 169-177<br>catenin alpha 1 | D13866 | SEQ ID-Nr. 45 |
| 46. EERIVELF | 306-313<br>signal transducer and activator of transcription 3 | BC000627 | SEQ ID-Nr. 46 |
| 47. EEIREAFRVF | 84-93<br>calmodulin 3 | J04046 | SEQ ID-Nr. 47 |
| 48. DEYIYRHFF | 344-352<br>cell cycle progression 8 protein | AF011794 | SEQ ID-Nr. 48 |
| 49. DELELHQRF | 308-316<br>adenovirus 5 E1A binding protein | X86098 | SEQ ID-Nr. 49 |
| 50. SEVKFTVTF | 80-88<br>galectin 2 | M87842 | SEQ ID-Nr. 50 |
| 51. IETIINTE | 12-19<br>calgranulin B | M26311 | SEQ ID-Nr. 51 |
| 52. KENPLQFKF | 61-69/72-80<br>villin 2 (ezrin)/(radixin) | 105021/<br>L02320 | SEQ ID-Nr. 52 |
| 53. DEVRTLTY | 41-48<br>hnRNP methyltransferase, *S. cerevisiae*-like 2 | Y10807 | SEQ ID-Nr. 53 |
| 54. GEAVVNRVF | 43-51<br>large multifunctional protease 2, LMP2 | Z14977 | SEQ ID Nr. 54 |

TABLE 1-continued

| Sequence | Position/Gene | Acc. No. | SEQ ID-No. |
|---|---|---|---|
| 55. EEVLIPDQKY | 385-394<br>F-box and leucine-rich repeat protein 3A | AF126028 | SEQ ID-Nv. 55 |
| 56. DEGRLVLEF | 163-171<br>sterol O-acyltransferase 1 | L21934 | SEQ ID-Nr. 56 |
| 57. DEVELIHF | 838-845<br>chromatin-specific transcription elongation factor | AF152961 | SEQ ID-Nr. 57 |
| 58. VEVLLNYAY | 83-91<br>NS1-binding protein | AF205218 | SEQ ID-Nr. 58 |
| 59. TENDIRVMF | 120-128<br>CUG triplet repeat, RNA-binding protein 1 | AF267534 | SEQ ID-Nr. 59 |
| 60. LEGLTVVY | 62-69<br>coatomer protein complex subunit zeta 1 | AF151878 | SEQ ID-Nr. 60 |
| 61. NELPTVAF | 192-199<br>hypothetical protein | AK001475 | SEQ ID-Nr. 61 |
| 62. EEFGQAFSF | 77-85<br>MHC, class II, DP alpha 1 | X03100 | SEQ ID-Nr. 62 |
| 63. VEAIFSKY | 33-40<br>hnRNP C (C1/C2) | M29063 | SEQ ID-Nr. 63 |
| 64. DERTFHIFY | 277-285<br>myosin, heavy polypeptide 10, non-muscle | M69181 | SEQ ID-Nr. 64 |
| 65. TEKVLAAVY | 206-214<br>aldolase B, fructose-bisphosphate | K01177 | SEQ ID-Nr. 65 |
| 66. VESPLSVSF | 159-167<br>hypothetical protein FLJ22318 | AK025971 | SEQ ID-Nr. 66 |
| 67. SEAGSHTLQW | MHC-I | | SEQ ID-Nr. 67 |
| 68. DEGKVIRF | 56-63<br>EST reading frame-1 | BF431469 | SEQ ID-Nr. 68 |
| Patient RCC13<br>HLA-A*02 | | | |
| 69. ALAAVVTEV | frameshift, DDX3 reading frame +2 | AF061337 | SEQ ID-Nr. 69 |
| 70. TLIEDILGV | 209-217<br>transient receptor protein 4 associated protein | AL132825 | SEQ ID-Nr. 70 |
| 71. ALFGALFLA | 2-10<br>phospholipid transfer protein | L26232 | SEQ ID-Nr. 71 |
| 72. VLATLVLLL | 72-80<br>EST | AA483794 | SEQ ID Nr. 72 |
| 73. TLDDLIAAV | 325-333<br>hypothetical protein FLJ10042 | AK000904 | SEQ ID-Nr. 73 |
| 74. YLDNGVVFV | 316-324<br>damage-specific DNA binding protein 1 (127 kD) | U18299 | SEQ ID-Nr. 74 |
| 75. SVFAGVVGV | 581-589<br>guanylate cyclase 1, soluble, alpha 3 | U58855 | SEQ ID-Nr. 75 |
| 76. SLINVGLISV | 48-57<br>acidic protein rich in leucines | BC000476 | SEQ ID-Nr. 76 |
| 77. ALADGVQKV | 176-184<br>apolipoprotein L, 1) | AF323540 | SEQ ID-Nr. 77 |

TABLE 1-continued

| Sequence | Position/Gene | Acc. No. | SEQ ID-No. |
|---|---|---|---|
| HLA-A*24 | | | |
| 78. TYGEIFEKF | 107-115 NADH dehydrogenase (ubiquinone) 1, (B14.5b) | AF070652 | SEQ ID-Nr. 78 |
| 79. YYMIGEQKF | 203-211 nicotinamide-n-methyltransferase | U08021 | SEQ ID-Nr. 79 |

The invention claimed is:

1. An isolated tumour-associated peptide comprising the amino acid sequence ALADGVQKV (SEQ ID NO: 77), the peptide having the ability to bind to a molecule of human major histocompatibility complex (MHC) class-I.

2. The peptide of claim 1 wherein the peptide is a marker for assessing a therapy course of a tumor disease.

3. The isolated peptide of claim 1, wherein said peptide consists of SEQ ID NO: 77.

4. The isolated peptide of claim 1, wherein said peptide consists of SEQ ID NO: 77 and one additional amino acid at the N-terminus or the C-terminus.

5. A pharmaceutical composition comprising the peptide of claim 1 and a pharmaceutically acceptable carrier.

6. A polynucleotide which encodes the peptide according to claim 1, such that a cell which has been transfected with said polynucleotide will produce said peptide.

7. A cell which has been genetically modified to contain a polynucleotide that encodes the peptide according to claim 1, and which cell will produce said peptide.

8. A cell which has been transfected with a polynucleotide that encodes the peptide according to claim 1, and which cell will produce said peptide.

9. A method of generating an immune response comprising administering to a subject in need thereof a pharmaceutical composition according to claim 5, wherein said immune response comprises a cytotoxic T-lymphocyte response to tumour cells.

10. The method of claim 9, wherein said subject suffers from a tumor disease selected from the group consisting of renal, breast, pancreas, gastric, bladder, and testis cancer.

11. A method of generating an immune response comprising administering to a subject in need thereof a composition comprising an adjuvant in combination with a peptide according to claim 1, wherein said immune response comprises a cytotoxic T-lymphocyte response to tumor cells.

12. A method of generating an immune response comprising administering to a subject in need thereof a peptide according to claim 1 which is bound to an antigen-presenting cell, wherein said immune response comprises a cytotoxic T-lymphocyte response to tumor cells.

13. A method of producing an antibody comprising:
  a) introducing the peptide of claim 1 into a subject,
  b) allowing said subject to generate an antibody response, and
  c) isolating said antibody from said subject.

* * * * *

SEQUENCE LISTING

<160> NUMBER OF SEQ ID NOS: 82

<210> SEQ ID NO 1
<211> LENGTH: 9
<212> TYPE: PRT
<213> ORGANISM: Homo sapiens

<400> SEQUENCE: 1

Tyr Val Asp Pro Val Ile Thr Ser Ile
1               5

<210> SEQ ID NO 2
<211> LENGTH: 9
<212> TYPE: PRT
<213> ORGANISM: Homo sapiens

<400> SEQUENCE: 2

Ser Val Ala Ser Thr Ile Thr Gly Val
1               5

<210> SEQ ID NO 3
<211> LENGTH: 9
<212> TYPE: PRT
<213> ORGANISM: Homo sapiens

<400> SEQUENCE: 3

Ala Leu Leu Asn Ile Lys Val Lys Leu
1               5

<210> SEQ ID NO 4
<211> LENGTH: 9
<212> TYPE: PRT
<213> ORGANISM: Homo sapiens

<400> SEQUENCE: 4

Ala Leu Phe Asp Gly Asp Pro His Leu
1               5

<210> SEQ ID NO 5
<211> LENGTH: 9
<212> TYPE: PRT
<213> ORGANISM: Homo sapiens

<400> SEQUENCE: 5

Arg Leu Leu Asp Tyr Val Val Asn Ile
1               5

<210> SEQ ID NO 6
<211> LENGTH: 9
<212> TYPE: PRT
<213> ORGANISM: Homo sapiens

```
<400> SEQUENCE: 6

Ala Leu Ala Asn Gly Ile Glu Glu Val
1               5

<210> SEQ ID NO 7
<211> LENGTH: 9
<212> TYPE: PRT
<213> ORGANISM: Homo sapiens

<400> SEQUENCE: 7

Gln Leu Ile Asp Lys Val Trp Gln Leu
1               5

<210> SEQ ID NO 8
<211> LENGTH: 9
<212> TYPE: PRT
<213> ORGANISM: Homo sapiens

<400> SEQUENCE: 8

Ala Leu Ser Asp Leu Glu Ile Thr Leu
1               5

<210> SEQ ID NO 9
<211> LENGTH: 9
<212> TYPE: PRT
<213> ORGANISM: Homo sapiens

<400> SEQUENCE: 9

Ile Leu Asp Thr Gly Thr Ile Gln Leu
1               5

<210> SEQ ID NO 10
<211> LENGTH: 10
<212> TYPE: PRT
<213> ORGANISM: Homo sapiens

<400> SEQUENCE: 10

Ser Leu Leu Gly Gly Asp Val Val Ser Val
1               5                   10

<210> SEQ ID NO 11
<211> LENGTH: 9
<212> TYPE: PRT
<213> ORGANISM: Homo sapiens

<400> SEQUENCE: 11

Phe Leu Asp Gly Asn Glu Leu Thr Leu
1               5

<210> SEQ ID NO 12
<211> LENGTH: 9
<212> TYPE: PRT
<213> ORGANISM: Homo sapiens

<400> SEQUENCE: 12

Asn Leu Leu Pro Lys Leu His Ile Val
1               5

<210> SEQ ID NO 13
<211> LENGTH: 9
<212> TYPE: PRT
<213> ORGANISM: Homo sapiens

<400> SEQUENCE: 13
```

```
Ala Leu Ala Ser His Leu Ile Glu Ala
1               5

<210> SEQ ID NO 14
<211> LENGTH: 9
<212> TYPE: PRT
<213> ORGANISM: Homo sapiens

<400> SEQUENCE: 14

Ser Leu Tyr Gly Gly Thr Ile Thr Ile
1               5

<210> SEQ ID NO 15
<211> LENGTH: 9
<212> TYPE: PRT
<213> ORGANISM: Homo sapiens

<400> SEQUENCE: 15

Phe Leu Leu Asp Lys Lys Ile Gly Val
1               5

<210> SEQ ID NO 16
<211> LENGTH: 9
<212> TYPE: PRT
<213> ORGANISM: Homo sapiens

<400> SEQUENCE: 16

Phe Leu Asp Gly Asn Glu Met Thr Leu
1               5

<210> SEQ ID NO 17
<211> LENGTH: 9
<212> TYPE: PRT
<213> ORGANISM: Homo sapiens

<400> SEQUENCE: 17

Ala Ile Val Asp Lys Val Pro Ser Val
1               5

<210> SEQ ID NO 18
<211> LENGTH: 10
<212> TYPE: PRT
<213> ORGANISM: Homo sapiens

<400> SEQUENCE: 18

Asp Val Ala Ser Val Ile Val Thr Lys Leu
1               5                   10

<210> SEQ ID NO 19
<211> LENGTH: 8
<212> TYPE: PRT
<213> ORGANISM: Homo sapiens

<400> SEQUENCE: 19

Leu Ala Ser Val Ser Thr Val Leu
1               5

<210> SEQ ID NO 20
<211> LENGTH: 9
<212> TYPE: PRT
<213> ORGANISM: Homo sapiens

<400> SEQUENCE: 20

Val Met Ala Pro Arg Thr Leu Val Leu
1               5
```

<210> SEQ ID NO 21
<211> LENGTH: 9
<212> TYPE: PRT
<213> ORGANISM: Homo sapiens

<400> SEQUENCE: 21

Leu Leu Phe Asp Arg Pro Met His Val
1               5

<210> SEQ ID NO 22
<211> LENGTH: 10
<212> TYPE: PRT
<213> ORGANISM: Homo sapiens

<400> SEQUENCE: 22

Met Thr Ser Ala Leu Pro Ile Ile Gln Lys
1               5                   10

<210> SEQ ID NO 23
<211> LENGTH: 10
<212> TYPE: PRT
<213> ORGANISM: Homo sapiens

<400> SEQUENCE: 23

Met Ala Gly Asp Ile Tyr Ser Val Phe Arg
1               5                   10

<210> SEQ ID NO 24
<211> LENGTH: 10
<212> TYPE: PRT
<213> ORGANISM: Homo sapiens

<400> SEQUENCE: 24

Glu Thr Ile Pro Leu Thr Ala Glu Lys Leu
1               5                   10

<210> SEQ ID NO 25
<211> LENGTH: 10
<212> TYPE: PRT
<213> ORGANISM: Homo sapiens

<400> SEQUENCE: 25

Asp Val Met Val Gly Pro Phe Lys Leu Arg
1               5                   10

<210> SEQ ID NO 26
<211> LENGTH: 9
<212> TYPE: PRT
<213> ORGANISM: Homo sapiens

<400> SEQUENCE: 26

Thr Ile Ile Asp Ile Leu Thr Lys Arg
1               5

<210> SEQ ID NO 27
<211> LENGTH: 9
<212> TYPE: PRT
<213> ORGANISM: Homo sapiens

<400> SEQUENCE: 27

Thr Ile Val Asn Ile Leu Thr Asn Arg
1               5

<210> SEQ ID NO 28
<211> LENGTH: 9

```
<212> TYPE: PRT
<213> ORGANISM: Homo sapiens

<400> SEQUENCE: 28

Thr Ile Ile Asp Ile Ile Thr His Arg
1               5

<210> SEQ ID NO 29
<211> LENGTH: 10
<212> TYPE: PRT
<213> ORGANISM: Homo sapiens

<400> SEQUENCE: 29

Ser Ile Phe Asp Gly Arg Val Val Ala Lys
1               5                   10

<210> SEQ ID NO 30
<211> LENGTH: 9
<212> TYPE: PRT
<213> ORGANISM: Homo sapiens

<400> SEQUENCE: 30

Ser Thr Ile Glu Tyr Val Ile Gln Arg
1               5

<210> SEQ ID NO 31
<211> LENGTH: 10
<212> TYPE: PRT
<213> ORGANISM: Homo sapiens

<400> SEQUENCE: 31

Glu Leu Ile Lys Pro Pro Thr Ile Leu Arg
1               5                   10

<210> SEQ ID NO 32
<211> LENGTH: 11
<212> TYPE: PRT
<213> ORGANISM: Homo sapiens

<400> SEQUENCE: 32

Glu Ile Ala Met Ala Thr Val Thr Ala Leu Arg
1               5                   10

<210> SEQ ID NO 33
<211> LENGTH: 9
<212> TYPE: PRT
<213> ORGANISM: Homo sapiens

<400> SEQUENCE: 33

Glu Thr Ile Gly Glu Ile Leu Lys Lys
1               5

<210> SEQ ID NO 34
<211> LENGTH: 9
<212> TYPE: PRT
<213> ORGANISM: Homo sapiens

<400> SEQUENCE: 34

Ser Leu Ala Asp Ile Met Ala Lys Arg
1               5

<210> SEQ ID NO 35
<211> LENGTH: 9
<212> TYPE: PRT
<213> ORGANISM: Homo sapiens
```

```
<400> SEQUENCE: 35

Glu Glu Ile Ala Phe Leu Lys Lys Leu
1               5

<210> SEQ ID NO 36
<211> LENGTH: 9
<212> TYPE: PRT
<213> ORGANISM: Homo sapiens

<400> SEQUENCE: 36

Asp Glu Ala Ala Phe Leu Glu Arg Leu
1               5

<210> SEQ ID NO 37
<211> LENGTH: 8
<212> TYPE: PRT
<213> ORGANISM: Homo sapiens

<400> SEQUENCE: 37

Asp Glu Met Lys Val Leu Val Leu
1               5

<210> SEQ ID NO 38
<211> LENGTH: 8
<212> TYPE: PRT
<213> ORGANISM: Homo sapiens

<400> SEQUENCE: 38

Asp Glu Val Lys Phe Leu Thr Val
1               5

<210> SEQ ID NO 39
<211> LENGTH: 9
<212> TYPE: PRT
<213> ORGANISM: Homo sapiens

<400> SEQUENCE: 39

Asn Glu Asn Ser Leu Phe Lys Ser Leu
1               5

<210> SEQ ID NO 40
<211> LENGTH: 8
<212> TYPE: PRT
<213> ORGANISM: Homo sapiens

<400> SEQUENCE: 40

Asp Glu Phe Lys Val Val Val Val
1               5

<210> SEQ ID NO 41
<211> LENGTH: 9
<212> TYPE: PRT
<213> ORGANISM: Homo sapiens

<400> SEQUENCE: 41

Glu Glu Val Lys Leu Ile Lys Lys Met
1               5

<210> SEQ ID NO 42
<211> LENGTH: 9
<212> TYPE: PRT
<213> ORGANISM: Homo sapiens

<400> SEQUENCE: 42

Asp Glu Val Lys Leu Pro Ala Lys Leu
```

```
1               5

<210> SEQ ID NO 43
<211> LENGTH: 9
<212> TYPE: PRT
<213> ORGANISM: Homo sapiens

<400> SEQUENCE: 43

Thr Glu Arg Glu Leu Lys Val Ala Tyr
1               5

<210> SEQ ID NO 44
<211> LENGTH: 10
<212> TYPE: PRT
<213> ORGANISM: Homo sapiens

<400> SEQUENCE: 44

Asn Glu Phe Ser Leu Lys Gly Val Asp Phe
1               5                   10

<210> SEQ ID NO 45
<211> LENGTH: 9
<212> TYPE: PRT
<213> ORGANISM: Homo sapiens

<400> SEQUENCE: 45

Asn Glu Gln Asp Leu Gly Ile Gln Tyr
1               5

<210> SEQ ID NO 46
<211> LENGTH: 8
<212> TYPE: PRT
<213> ORGANISM: Homo sapiens

<400> SEQUENCE: 46

Glu Glu Arg Ile Val Glu Leu Phe
1               5

<210> SEQ ID NO 47
<211> LENGTH: 10
<212> TYPE: PRT
<213> ORGANISM: Homo sapiens

<400> SEQUENCE: 47

Glu Glu Ile Arg Glu Ala Phe Arg Val Phe
1               5                   10

<210> SEQ ID NO 48
<211> LENGTH: 9
<212> TYPE: PRT
<213> ORGANISM: Homo sapiens

<400> SEQUENCE: 48

Asp Glu Tyr Ile Tyr Arg His Phe Phe
1               5

<210> SEQ ID NO 49
<211> LENGTH: 9
<212> TYPE: PRT
<213> ORGANISM: Homo sapiens

<400> SEQUENCE: 49

Asp Glu Leu Glu Leu His Gln Arg Phe
1               5
```

```
<210> SEQ ID NO 50
<211> LENGTH: 9
<212> TYPE: PRT
<213> ORGANISM: Homo sapiens

<400> SEQUENCE: 50

Ser Glu Val Lys Phe Thr Val Thr Phe
1               5

<210> SEQ ID NO 51
<211> LENGTH: 8
<212> TYPE: PRT
<213> ORGANISM: Homo sapiens

<400> SEQUENCE: 51

Ile Glu Thr Ile Ile Asn Thr Phe
1               5

<210> SEQ ID NO 52
<211> LENGTH: 9
<212> TYPE: PRT
<213> ORGANISM: Homo sapiens

<400> SEQUENCE: 52

Lys Glu Asn Pro Leu Gln Phe Lys Phe
1               5

<210> SEQ ID NO 53
<211> LENGTH: 8
<212> TYPE: PRT
<213> ORGANISM: Homo sapiens

<400> SEQUENCE: 53

Asp Glu Val Arg Thr Leu Thr Tyr
1               5

<210> SEQ ID NO 54
<211> LENGTH: 9
<212> TYPE: PRT
<213> ORGANISM: Homo sapiens

<400> SEQUENCE: 54

Gly Glu Ala Val Val Asn Arg Val Phe
1               5

<210> SEQ ID NO 55
<211> LENGTH: 10
<212> TYPE: PRT
<213> ORGANISM: Homo sapiens

<400> SEQUENCE: 55

Glu Glu Val Leu Ile Pro Asp Gln Lys Tyr
1               5                   10

<210> SEQ ID NO 56
<211> LENGTH: 9
<212> TYPE: PRT
<213> ORGANISM: Homo sapiens

<400> SEQUENCE: 56

Asp Glu Gly Arg Leu Val Leu Glu Phe
1               5

<210> SEQ ID NO 57
<211> LENGTH: 8
<212> TYPE: PRT
```

<213> ORGANISM: Homo sapiens

<400> SEQUENCE: 57

Asp Glu Val Glu Leu Ile His Phe
1               5

<210> SEQ ID NO 58
<211> LENGTH: 9
<212> TYPE: PRT
<213> ORGANISM: Homo sapiens

<400> SEQUENCE: 58

Val Glu Val Leu Leu Asn Tyr Ala Tyr
1               5

<210> SEQ ID NO 59
<211> LENGTH: 9
<212> TYPE: PRT
<213> ORGANISM: Homo sapiens

<400> SEQUENCE: 59

Thr Glu Asn Asp Ile Arg Val Met Phe
1               5

<210> SEQ ID NO 60
<211> LENGTH: 8
<212> TYPE: PRT
<213> ORGANISM: Homo sapiens

<400> SEQUENCE: 60

Leu Glu Gly Leu Thr Val Val Tyr
1               5

<210> SEQ ID NO 61
<211> LENGTH: 8
<212> TYPE: PRT
<213> ORGANISM: Homo sapiens

<400> SEQUENCE: 61

Asn Glu Leu Pro Thr Val Ala Phe
1               5

<210> SEQ ID NO 62
<211> LENGTH: 9
<212> TYPE: PRT
<213> ORGANISM: Homo sapiens

<400> SEQUENCE: 62

Glu Glu Phe Gly Gln Ala Phe Ser Phe
1               5

<210> SEQ ID NO 63
<211> LENGTH: 8
<212> TYPE: PRT
<213> ORGANISM: Homo sapiens

<400> SEQUENCE: 63

Val Glu Ala Ile Phe Ser Lys Tyr
1               5

<210> SEQ ID NO 64
<211> LENGTH: 9
<212> TYPE: PRT
<213> ORGANISM: Homo sapiens

<400> SEQUENCE: 64

```
Asp Glu Arg Thr Phe His Ile Phe Tyr
1               5

<210> SEQ ID NO 65
<211> LENGTH: 9
<212> TYPE: PRT
<213> ORGANISM: Homo sapiens

<400> SEQUENCE: 65

Thr Glu Lys Val Leu Ala Ala Val Tyr
1               5

<210> SEQ ID NO 66
<211> LENGTH: 9
<212> TYPE: PRT
<213> ORGANISM: Homo sapiens

<400> SEQUENCE: 66

Val Glu Ser Pro Leu Ser Val Ser Phe
1               5

<210> SEQ ID NO 67
<211> LENGTH: 10
<212> TYPE: PRT
<213> ORGANISM: Homo sapiens

<400> SEQUENCE: 67

Ser Glu Ala Gly Ser His Thr Leu Gln Trp
1               5                   10

<210> SEQ ID NO 68
<211> LENGTH: 8
<212> TYPE: PRT
<213> ORGANISM: Homo sapiens

<400> SEQUENCE: 68

Asp Glu Gly Lys Val Ile Arg Phe
1               5

<210> SEQ ID NO 69
<211> LENGTH: 9
<212> TYPE: PRT
<213> ORGANISM: Homo sapiens

<400> SEQUENCE: 69

Ala Leu Ala Ala Val Val Thr Glu Val
1               5

<210> SEQ ID NO 70
<211> LENGTH: 9
<212> TYPE: PRT
<213> ORGANISM: Homo sapiens

<400> SEQUENCE: 70

Thr Leu Ile Glu Asp Ile Leu Gly Val
1               5

<210> SEQ ID NO 71
<211> LENGTH: 9
<212> TYPE: PRT
<213> ORGANISM: Homo sapiens

<400> SEQUENCE: 71

Ala Leu Phe Gly Ala Leu Phe Leu Ala
1               5
```

<210> SEQ ID NO 72
<211> LENGTH: 9
<212> TYPE: PRT
<213> ORGANISM: Homo sapiens

<400> SEQUENCE: 72

Val Leu Ala Thr Leu Val Leu Leu Leu
1               5

<210> SEQ ID NO 73
<211> LENGTH: 9
<212> TYPE: PRT
<213> ORGANISM: Homo sapiens

<400> SEQUENCE: 73

Thr Leu Asp Asp Leu Ile Ala Ala Val
1               5

<210> SEQ ID NO 74
<211> LENGTH: 9
<212> TYPE: PRT
<213> ORGANISM: Homo sapiens

<400> SEQUENCE: 74

Tyr Leu Asp Asn Gly Val Val Phe Val
1               5

<210> SEQ ID NO 75
<211> LENGTH: 9
<212> TYPE: PRT
<213> ORGANISM: Homo sapiens

<400> SEQUENCE: 75

Ser Val Phe Ala Gly Val Val Gly Val
1               5

<210> SEQ ID NO 76
<211> LENGTH: 10
<212> TYPE: PRT
<213> ORGANISM: Homo sapiens

<400> SEQUENCE: 76

Ser Leu Ile Asn Val Gly Leu Ile Ser Val
1               5                   10

<210> SEQ ID NO 77
<211> LENGTH: 9
<212> TYPE: PRT
<213> ORGANISM: Homo sapiens

<400> SEQUENCE: 77

Ala Leu Ala Asp Gly Val Gln Lys Val
1               5

<210> SEQ ID NO 78
<211> LENGTH: 9
<212> TYPE: PRT
<213> ORGANISM: Homo sapiens

<400> SEQUENCE: 78

Thr Tyr Gly Glu Ile Phe Glu Lys Phe
1               5

<210> SEQ ID NO 79

```
<211> LENGTH: 9
<212> TYPE: PRT
<213> ORGANISM: Homo sapiens

<400> SEQUENCE: 79

Tyr Tyr Met Ile Gly Glu Gln Lys Phe
1               5

<210> SEQ ID NO 80
<211> LENGTH: 10
<212> TYPE: PRT
<213> ORGANISM: Homo sapiens

<400> SEQUENCE: 80

Glu Leu Thr Leu Gly Glu Phe Leu Lys Leu
1               5                   10

<210> SEQ ID NO 81
<211> LENGTH: 9
<212> TYPE: PRT
<213> ORGANISM: Human Immunodeficiency Virus

<400> SEQUENCE: 81

Ile Leu Lys Glu Pro Val His Gly Val
1               5

<210> SEQ ID NO 82
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ile, Val, or Met
<220> FEATURE:
<221> NAME/KEY: MISC_FEATURE
<222> LOCATION: (9)..(9)
<223> OTHER INFORMATION: Xaa = Val, Ile, or Ala

<400> SEQUENCE: 82

Ser Xaa Ala Ser Thr Ile Thr Gly Xaa
1               5
```